(12) United States Patent
Estenfelder et al.

(10) Patent No.: US 8,513,470 B2
(45) Date of Patent: Aug. 20, 2013

(54) PROCESS FOR OXIDATION ON FIXED CATALYTIC BED OF METHANOL TO FORMALDEHYDE

(75) Inventors: Marvin Estenfelder, Ebersberg (DE); Roberto Zaino, Villabella (IT)

(73) Assignee: Süd-Chemie, Catalysts Italia S.r.l., Novara (IT)

( * ) Notice: Subject to any disclaimer, the term of this patent is extended or adjusted under 35 U.S.C. 154(b) by 120 days.

(21) Appl. No.: 13/142,689

(22) PCT Filed: Dec. 18, 2009

(86) PCT No.: PCT/EP2009/067559
§ 371 (c)(1),
(2), (4) Date: Jun. 29, 2011

(87) PCT Pub. No.: WO2010/076246
PCT Pub. Date: Jul. 8, 2010

(65) Prior Publication Data
US 2011/0269998 A1    Nov. 3, 2011

(30) Foreign Application Priority Data

Dec. 29, 2008  (IT) .............................. MI2008A2332

(51) Int. Cl.
*C07C 45/38*  (2006.01)

(52) U.S. Cl.
USPC .......................................... 568/472; 568/474

(58) Field of Classification Search
USPC .................................................. 568/472, 474
See application file for complete search history.

(56) References Cited

U.S. PATENT DOCUMENTS

| 6,552,233 | B2 * | 4/2003 | Wachs et al. .................. 568/471 |
| 2002/0055659 | A1 | 5/2002 | Wachs et al. |
| 2003/0171624 | A1 | 9/2003 | Wachs et al. |

FOREIGN PATENT DOCUMENTS

WO    WO 02/22539 A2    3/2002

OTHER PUBLICATIONS

International Search Report dated May 20, 2010 issued in PCT/EP2009/067559.

* cited by examiner

*Primary Examiner* — Sikarl Witherspoon
(74) *Attorney, Agent, or Firm* — Scully, Scott, Murphy & Presser, P.C.

(57) ABSTRACT

A process for the fixed bed oxidation of methanol to formaldehyde wherein the bed comprises at least two layers having different catalytic activity, wherein the layer of lower activity is comprised in the part of the bed from which the reactant gas mixture enters and its activity is calibrated so that the maximum hot spot temperature in the layer is comprised between 350° C. and 430° C. and is higher than the maximum hot spot temperature of the layer of greater activity formed by pure catalyst, and wherein during the period in which the situation of the maximum hot spot temperature of the layer of lower activity remains at the values cited above, the conversion of methanol is higher than 96% by mols.

24 Claims, No Drawings

PROCESS FOR OXIDATION ON FIXED CATALYTIC BED OF METHANOL TO FORMALDEHYDE

TECHNICAL FIELD

The present invention relates to an improved process for the production of formaldehyde by catalytic oxidation of methanol on a bed formed by at least two layers having different catalytic activity, wherein the catalytic activity of the layer comprised in the part of the bed at the inlet of the reactant gases is calibrated so as to obtain, in said layer, a maximum hot spot temperature that is comprised in a higher critical range than used in processes known so far and is higher than the maximum hot spot temperature of the layer of greater activity formed by pure catalyst. During said situation of maximum hot spot temperatures, methanol conversion is higher than 96% by mols.

BACKGROUND ART

Currently known processes for the production of formaldehyde by oxidation of methanol on a catalytic bed formed by two or more layers having different catalytic activity use the layer of lower activity, formed by mixtures of pure catalyst with inert material which is by far more diluted and longer than in previous processes in order to have relatively low maximum hot spot temperatures in this layer, generally comprised between 330° C. and 350° C. These temperatures, after a short period of activity of the layer, tend to decrease and in the final steps become lower than in the layer formed by pure catalyst.

By working under such conditions, the life of the catalyst decreases significantly. The decrease requires frequent reloading of the catalyst in the tubes of the tube bundle, an operation which is long and expensive and causes frequent stops of the plant. Moreover, there is the need to recover the molybdenum from the spent catalyst, imposed by the high price currently reached by this metal.

OBJECTS

The object of the present invention is to provide a fixed catalytic bed to be used in processes for the production of formaldehyde by catalytic oxidation of methanol capable of providing high formaldehyde yields without compromising the life of the catalyst.

Other objects will become evident from the description of the invention.

DESCRIPTION OF THE INVENTION

It has now been found unexpectedly that it is possible to obtain high formaldehyde yields and maintain a sufficiently long life of the catalyst used in the fixed catalytic bed comprising at least two layers having different catalytic activity, used in processes for the production of formaldehyde by catalytic oxidation of methanol, if the activity of the layer of lower activity comprised within the part of the bed from which the reactant gas mixture enters is calibrated so as to obtain a maximum hot spot temperature in said layer comprised in the range from 350° C. to 430° C., and higher than the maximum hot spot temperature present in the layer of greater catalytic activity formed by pure catalyst. In the period during which the maximum hot spot temperature remains at the values cited above, methanol conversion is higher than 96% by mols.

The situation of the maximum hot spot temperatures cited above lasts for at least 50% of the total life of the catalyst, more precisely at least 80%.

The maximum hot spot temperature of the layer of lower catalytic activity is comprised between 360° C. and 410° C. and the maximum hot spot temperature difference of the two layers is from 30° C. to 90° C., in the steps of the process in which methanol conversion is highest.

Maximum hot spot temperatures in the layer of lower activity higher than 430° C. are not usable due to catalyst sintering phenomena, which rapidly and drastically lower the activity of the catalyst.

The less active catalytic layer is formed by pure catalyst diluted with inert material or by catalyst with lower activity than the catalyst used in the layer of greater activity.

The catalyst that is present in the layer of greater activity can be more active than the catalyst used in the layer of lower activity and the activity of the more active layer is calibrated by acting on the activity of the catalyst.

The less active catalyst can be obtained by acting on the surface area (BET) of the catalyst, for example by performing calcination at relatively higher temperatures, at which the surface area decreases and/or the geometry of the catalyst can be changed. The less active catalyst can have the same composition as the catalyst of the more active layer or a different one. In both cases, the activity of the layers is calibrated so that the maximum hot spot temperature of the layer of lower activity conforms to the maximum hot spot temperature according to the invention.

The catalytic activity of the layer of lower activity is preset to the desired value by acting on the degree of dilution of the layer and/or on its length, or on the activity of the less active catalyst.

The maximum hot spot temperature of the less active layer decreases over time and shifts toward the layer of greater activity until it becomes similar to that temperature and then lower in the final step of the life of the catalyst.

The length of the layer of lower activity is generally 20-60% of the length of the catalytic bed, preferably 40-60%.

The maximum hot spot temperature of this layer depends on various factors and mainly, besides the catalytic activity of the layer, also on the inlet concentration of methanol, on the linear velocity of the gas mixture and on the pressure. The higher the concentration of the methanol and the pressure, the higher the maximum hot spot temperature; said temperature decreases as the linear velocity increases. Once these parameters have been set, the most suitable catalytic activity is determined experimentally.

The standard test for determining catalytic activity is as follows. 50 cm of granules of pure or diluted or less active catalyst are loaded into an AISI 316 stainless steel tube with an inside diameter of 23 mm. The temperature of the cooling liquid is set at 250° C. The inlet concentration of the methanol is 6% by volume, the oxygen concentration is 10% by volume, the remainder is nitrogen. Linear velocity is 1 Nm/s and the pressure is 1.2 bar abs. After 24 h, methanol conversion is measured: the higher the conversion, the higher the catalytic activity of the layer.

The catalyst to be used in the various layers is in form of granules having a definite geometric configuration, preferably a hollow cylindrical shape with one or more through bores. Cylindrical shapes with a trilobed circular cross-section, with lobes provided with through bores which are parallel to the axis of the granule, can be used conveniently. The geometric shapes of the inert material, which is generally ceramic or metallic, are similar to those of the catalyst.

The operating conditions of the methanol oxidation process are the known ones: the inlet concentration by volume of the oxygen and of the methanol is 6-21%, preferably 8-12% and more preferably 9-11%, and 6-12%, respectively; the linear velocity of the gas mixture is 0.8-3.0 Nm/s, the pressure is 1-3 bar abs, preferably 1-2.3 bar abs, the temperature of the reactant gas mixture is 90° C.-200° C. at inlet, preferably 110° C.-160° C. The temperature of the cooling liquid is between 240° C. and 330° C., preferably 250°-320°.

The process is carried out in a bundle-tube reactor, the tubes of which are immersed in a circulating cooling liquid formed of oil, fused salts or any other highly boiling liquid suitable to heat transfer.

The catalyst normally used in fixed bed methanol oxidation processes comprises compositions having the formula $Fe_2(MoO_3)_4/MoO_3$, in which the Mo/Fe ratio is comprised between 1 and 6, preferably 2-3.

A convenient method of preparing the catalyst which allows to obtain a catalyst free from damaging impurities, such as sodium and chloride ions, consists of the reaction between powdered iron and $MoO_3$ in an aqueous medium and subsequent or simultaneous oxidation of the reaction product. The method is described in EP 1 674 156.

The catalyst can be added with cerium molybdate in a quantity of 0.1-10% by weight as a stabilizer (EP 1 674 155).

Another catalyst used for oxidation of methanol to formaldehyde is constituted by $V_2O_5$ supported on carriers such as $TiO_2$, $Al_2O_3$, $ZrO_2$, $SiO_2$ and SiC. This catalyst can be used in a mixture with the catalyst based on $Fe_2(MoO_4)_3/MoO_3$ preferably in the layer of greater activity.

The following examples are given by way of non-limiting illustration of the scope of the invention.

Example 1

A tube made of AISI 316 steel with an inside diameter of 21 mm is formed by 2 layers of inert material and/or catalyst. The first layer (from the top downward) is formed by 50 cm of granules of catalyst diluted at 50% by volume with granules of inert ceramic material; the second layer (from the top downward) is formed by 50 cm of granules of pure catalyst.

A stainless steel sheath is arranged axially within the tube and has an outside diameter of 3 mm; a thermocouple is made to slide therein to measure the axial temperature profile of the catalytic bed.

The reactant gases flow downward from above.

The temperature of the bath of fused salts is set to 271° C.

The concentration by volume of the methanol and of the oxygen at inlet is 10% and 9.5%, respectively.

The linear velocity of the gas at inlet is equal to 1.5 Nm/s and the pressure is 1.3 abs bar.

The temperature of the mixture of reactant gases at inlet is 140° C.

After 6 days, the conversion of the methanol is 98.6% by mols and the formaldehyde yield is 93.8% by mols. The maximum hot spot temperature of the diluted layer is 390° C., the maximum hot spot temperature of the pure catalyst layer is 315° C.

After 6 months of operation, the maximum hot spot temperature in the diluted layer has decreased to 354° C. and the maximum hot spot temperature of the pure catalyst is 340° C. The temperature of the bath of fused salts is 295° C. Conversion of methanol is 98.7% by mols and formaldehyde yield is 93.1% by mols.

Comparison Example 1

One proceeds in the same conditions as example 1, except for the second layer of diluted catalyst, in which the diluent concentration is 75% by volume and except for the temperature of the bath of fused salts, which is 276° C. After a few days (the same days as Example 1), the maximum hot spot temperature of the diluted layer is 346° C. and the maximum hot spot temperature of the pure catalyst layer is 344° C.

Methanol conversion is 98.5% by mols; formaldehyde yield is 93.0% by mols.

After 6 months, the temperature of the fused salt bath is 304° C., the maximum hot spot temperature of the diluted layer is 339° C., the maximum hot spot temperature of the pure catalyst layer is 360° C.

Methanol conversion is 98.6%; formaldehyde yield is 92.1%.

After 6 months, reversal of the difference between the maximum hot spot temperature in the diluted layer and the maximum hot spot temperature of the pure catalyst layer is observed, indicating high deactivation in progress in the catalyst of the diluted layer.

DEFINITIONS

By "maximum hot spot temperature" it is meant a relative or absolute maximum in the curve obtained by measuring the axial temperature profile of the catalytic bed, whose second derivative is zero.

By "total catalyst life" it is meant the period of time under flow of reactants that elapses between the beginning of the operation of the reactor after loading the fresh catalyst and the halting of the reactor followed by the unloading of the spent catalyst.

The disclosures in Italian Patent Application No. MI2008A002332 from which this application claims priority are incorporated herein by reference.

The invention claimed is:

1. A process for the fixed bed oxidation of methanol to formaldehyde
wherein the catalytic bed comprises at least two layers having different catalytic activity, of which the layer of lower activity is comprised within the part of the bed from which the reactant gas mixture enters, and its activity is calibrated to obtain in the hot spot zone of the layer a maximum hot spot temperature comprised in the range from 350° C. to 430° C., and being higher than the maximum hot spot temperature present in the layer of greater activity wherein, during the period of said situation of the maximum hot spot temperature, the conversion of methanol is higher than 96% by mols, and wherein the catalyst used in the layers of different catalytic activity is a molybdate of formula $Fe_2(MoO_4)_3/MoO_3$, wherein the Mo/Fe ratio is from 1 to 6.

2. The process of claim 1, wherein the situation of the maximum temperatures of hot spot lasts for at least 50% of the total life of the catalyst.

3. The process of claim 1, wherein the situation of the maximum temperatures of hot spot lasts for at least 80% of the total catalyst life.

4. The process of claim 1, wherein the maximum hot spot temperature of the lower activity layer is from 360° C. to 410° C., and is from 30° C. to 90° C. higher than the maximum hot spot temperature of the greater activity layer; said situation occurs in the steps of the process wherein the conversion of methanol is higher.

5. The process according to claim 1, wherein the layer of lower catalytic activity is formed of a mixture of pure catalyst and inert material, and the layer of higher activity is formed of pure catalyst.

6. The process of claim 5, wherein the catalytic activity of the lower activity layer is calibrated by acting on the degree of dilution of the pure catalyst, and/or the length of the layer.

7. The process according to claim 1, wherein the layer of lower catalyst activity is formed of a catalyst having the same or different composition with respect to the pure catalyst of the higher activity layer but is less active and the activity of the less active layer is calibrated by acting on the activity of said less active catalyst.

8. The process according to claim 1, wherein the layer of greater activity is formed of catalyst having the same or different composition with respect to the catalyst comprised in the layer of lower activity but is more active and the activity of the layer is calibrated acting on the activity of the more active catalyst.

9. The process according to claim 1, wherein the difference of activity between the layer of lower activity and that of greater activity is due to different surface area (BET) and/or to different catalyst geometry.

10. The process according to claim 1, wherein the length of the lower activity layer is 20-60% the length of the catalytic bed.

11. The process of claim 10, wherein the height of the lower activity layer is 40-60% the height of the catalytic bed.

12. The process according to claim 1, wherein the inlet temperature of the reactant gas mixture is from 90° C. to 200° C.

13. The process of claim 12, wherein the inlet temperature is from 110° C. to 160° C.

14. The process according to claim 1, carried out in a bundle-tube reactor, the tubes of which are immersed in a circulating coolant liquid formed of oil, fused salts or any other highly boiling liquid suitable to heat transfer.

15. The process according to claim 14, wherein the temperature of the coolant liquid is from 240° C. to 330° C.

16. The process of claim 15, wherein the temperature of the coolant liquid is from 250° C.-320° C.

17. The process according to claim 1, wherein methanol and oxygen are employed in concentration by volume at inlet from 6 to 12% and 6 to 21% respectively, the linear velocity of the gas flow is 0.8-3 Nm/sec, and the pressure 1-3 bar abs.

18. The process of claim 17, wherein the concentration of methanol is 8-12% by volume.

19. The process of claim 18, wherein the concentration of methanol is 9-11% by volume.

20. The process of claim 17, wherein the pressure is 1-2.3 bar abs.

21. The process according to claim 1, wherein the catalyst and the inert material are in form of hollow granules having definite geometric configuration.

22. The process according to claim 21, wherein the hollow granules are in cylindrical form having circular trilobed cross-section in which the lobes are provided with through bores parallel to the axis of the granule.

23. The process according to claim 1, wherein the catalyst is the product of reaction of iron powder with $MoO_3$ in aqueous medium and oxidation of the resultant product.

24. The process according to claim 1, wherein the catalyst contains cerium molybdate in quantity of 0.1-10 wt %.

* * * * *